(12) United States Patent
Stenzel et al.

(10) Patent No.: US 10,569,074 B2
(45) Date of Patent: Feb. 25, 2020

(54) MEDICAL COUPLING AND MEDICAL SYSTEM COMPRISING MEDICAL COUPLING

(71) Applicant: B. BRAUN AVITUM AG, Melsungen (DE)

(72) Inventors: Bruno Stenzel, Münden (DE);
Sebastian Brögger, Knüllwald (DE);
Uta Ludwig, Wehretal (DE)

(73) Assignee: B. Braun Avitum AG (DE)

( * ) Notice: Subject to any disclaimer, the term of this patent is extended or adjusted under 35 U.S.C. 154(b) by 89 days.

(21) Appl. No.: 15/410,160

(22) Filed: Jan. 19, 2017

(65) Prior Publication Data

US 2017/0216572 A1  Aug. 3, 2017

(30) Foreign Application Priority Data

Feb. 3, 2016 (DE) .................. 10 2016 101 911

(51) Int. Cl.
*A61M 39/10* (2006.01)
*A61M 39/00* (2006.01)

(52) U.S. Cl.
CPC ......... *A61M 39/1011* (2013.01); *A61M 39/00* (2013.01); *A61M 39/10* (2013.01); *A61M 2039/1027* (2013.01); *A61M 2039/1044* (2013.01); *A61M 2039/1077* (2013.01)

(58) Field of Classification Search
CPC .. A61M 39/1011; A61M 39/00; A61M 39/10; A61M 2039/1016; A61M 2039/1044; A61M 2039/1027; A61M 2039/1077; F16L 27/0808
See application file for complete search history.

(56) References Cited

U.S. PATENT DOCUMENTS

| 7,455,325 B2 | 11/2008 | Mejlhede et al. |
| 7,878,552 B2 * | 2/2011 | Freter ............... F16L 37/098 285/308 |
| 8,157,296 B2 * | 4/2012 | Ullrich ............... F16L 37/098 285/321 |

(Continued)

FOREIGN PATENT DOCUMENTS

| DE | 602004003477 T2 | 10/2007 |
| EP | 1599249 B1 | 11/2006 |

(Continued)

OTHER PUBLICATIONS

German Search Report for German Application No. 10 2016 101 911.9, dated Sep. 26, 2016, with English translation—14 Pages.

(Continued)

*Primary Examiner* — Bradley J Osinski
(74) *Attorney, Agent, or Firm* — RatnerPrestia

(57) ABSTRACT

A coupling for fluid-tight connection of two fluid-guiding portions in medical applications. The coupling is an axially lockable quick-connect coupling and comprises a male coupling portion having a continuous first passage and a female coupling portion adapted to be slipped over the male coupling portion and having a continuous second passage. A preferably circumferential radial sealing is provided on the outer periphery of the male coupling portion and/or on the inner periphery of the female coupling portion.

11 Claims, 3 Drawing Sheets

(56) References Cited

U.S. PATENT DOCUMENTS

| | | | |
|---|---|---|---|
| 2002/0010437 A1* | 1/2002 | Lopez | A61M 39/1011 |
| | | | 604/256 |
| 2005/0020980 A1* | 1/2005 | Inoue | A61M 5/14244 |
| | | | 604/152 |
| 2005/0101939 A1 | 5/2005 | Mitchell | |
| 2005/0256461 A1* | 11/2005 | DiFiore | A61M 25/0075 |
| | | | 604/247 |
| 2006/0217683 A1* | 9/2006 | Patania | A61M 16/08 |
| | | | 604/533 |
| 2006/0293640 A1* | 12/2006 | Greco | A61J 1/2096 |
| | | | 604/411 |
| 2008/0065000 A1 | 3/2008 | Bidinger et al. | |
| 2009/0188575 A1* | 7/2009 | Williams | F16L 37/0985 |
| | | | 137/798 |
| 2010/0036329 A1 | 2/2010 | Razack | |
| 2011/0095528 A1 | 4/2011 | Forberg | |
| 2015/0005715 A1* | 1/2015 | Cowan | A61M 39/10 |
| | | | 604/241 |

FOREIGN PATENT DOCUMENTS

| | | |
|---|---|---|
| EP | 1731128 A1 | 12/2006 |
| EP | 2138202 A1 | 12/2009 |
| GB | 2091364 A | 7/1982 |
| WO | 2006039501 A2 | 4/2006 |

OTHER PUBLICATIONS

European Search Report with English language translation for Application No. 17151781.6, dated Jul. 7, 2017, 18 pages.

* cited by examiner

MEDICAL COUPLING AND MEDICAL SYSTEM COMPRISING MEDICAL COUPLING

CROSS REFERENCE TO RELATED APPLICATIONS

This application claims priority to German application DE 10 2016 101 911.9 filed Feb. 3, 2016, the contents of such application being incorporated by reference herein.

FIELD OF THE INVENTION

The present invention relates to a medical coupling for fluid-tight connection of two fluid-guiding portions in medical applications which preferably enable an extracorporeal bloodline system to be connected to a dialyzer as well as to a machine for extracorporeal blood treatment and relates to a medical system comprising a medical coupling.

BACKGROUND OF THE INVENTION

In extracorporeal blood treatment or else renal replacement therapy the blood taken from the patient is continuously guided outside the body within a circulation through a dialyzer and is supplied to the patient again. For this, the extracorporeal bloodline system guiding the blood of the patient has to be connected to the dialyzer. This connection is frequently realized via a Luer lock.

DESCRIPTION OF THE RELATED ART

For example, from DE 60 2004 003 477 T2 a medical connector for connecting a tube to a medical device is known. Said connector includes, at one of its ends, a Luer lock via which it can be connected to the medical device. At its other end the connector is tightly connected to the tube or, respectively, the tube is glued into the connector.

In systems in which bloodlines are connected via a Luer lock to a medical device such as a dialyzer the following problems may arise. For example, frequently the bloodline may be twisted and often this results in the screwed connection becoming unscrewed, which is not detected. This drawback has technical reasons, as the Luer lock of the dialyzer is not tightly connected to the tube. The heat expansion of the Luer locks may entail decrease of the friction and, respectively, the self-locking of the thread. The tight connection of the tube to the Luer lock may cause the tube to exert a permanent loosening torque on the thread. Further, the quality of the screwed connection is dependent on the operator. In the course of therapy, the connection therefore has to be checked for correct fitting and has to be corrected, if necessary, by the operating staff.

SUMMARY OF THE INVENTION

Consequently, it is an object of the present invention to provide a coupling which ensures that tubes or bloodlines do not twist and which provides a connection torque independent of the user as well as avoids time consuming checking and correction of the connection.

This object is achieved by a medical coupling comprising the features of the independent claim as well as by a medical system. Advantageous further developments are described in the subclaims.

The medical (fluid) coupling according to aspects of the invention for fluid-tight connection of (at least) two fluid-guiding portions in medical applications is designed as an axially lockable quick-connect coupling and includes a male coupling portion having a continuous first passage and a female coupling portion adapted to be slipped over the male coupling portion and having a continuous second passage. In addition, on the outer periphery of the male coupling portion and/or on the inner periphery of the female coupling portion a preferably circumferential radial sealing is provided.

Hence the medical coupling according to aspects of the invention enables, for instance, a fluid line and a medical apparatus or else two fluid lines, as examples of fluid-guiding portions, to be easily connected to each other. The coupling is obtained by connecting a male coupling portion and a female coupling portion. Accordingly, the male coupling portion is configured as a type of cylindrical projection including a continuous internal passage. The female coupling portion is a type of sleeve in which the male coupling portion can be partly or completely accommodated.

For connection, the female coupling portion is slipped in the axial direction of the sleeve or, respectively, of the cylindrical projection over the male coupling portion. In so doing, the two coupling portions are (permanently) engaged in each other. When used in renal replacement therapy, for example the extracorporeal bloodline system and the dialyzer will not be separated any more after therapy. Therefore a permanent connection is not detrimental. In addition, the radial sealing formed between the male and female coupling portions ensures that the two coupling portions and thus the two fluid-guiding portions are interconnected in a sealing manner.

By the coupling designed in this way a connection of two fluid-guiding portions can be quickly and easily achieved. For this purpose, no additional securing elements are required. Moreover, time-consuming screwing or rotation of the two coupling portions relative to each other is dispensed with. The connection thus is also safer because the two coupling portions cannot independently become undone or unscrewed from each other. Moreover, due to the radial sealing rotation about the longitudinal axis of the coupling of the female coupling portion relative to the male coupling portion is possible.

According to one aspect of the invention, the male coupling portion may be formed integrally with a medical apparatus or a medical device, especially a dialyzer or a machine for extracorporeal blood treatment.

In this way, no additional components are required for connection to the medical apparatus and thus a simple, inexpensive configuration involving few components is possible.

In accordance with one aspect of the invention, the male coupling portion may include a first fastening portion.

In accordance with one aspect of the invention the male coupling portion may be adapted to be fastened to a medical apparatus via the first fastening portion.

In accordance with one aspect of the invention, the first fastening portion of the male coupling portion may be a Luer lock adapted which is connectable to a Luer lock of the medical apparatus.

In accordance with one aspect of the invention, the first fastening portion of the male coupling portion may be a Luer lock having a female internal cone which is connectable to a male external cone of the medical apparatus.

By connecting the male coupling portion via the first fastening portion to the medical apparatus it is possible to use the coupling according to aspects of the invention for already existing medical apparatuses, too. In other words, the male coupling portion may be screwed, as a kind of adapter, onto a Luer lock of the medical apparatus, for example, and thus the male coupling portion connects the medical apparatus to the female coupling portion.

In accordance with one aspect of the invention, the first fastening portion of the male coupling portion may be in the form of an internal thread portion that is adapted to be connected to an external thread portion of the medical apparatus.

Thus, for instance, the male coupling portion may be part of the cover of the medical apparatus which can be screwed onto a housing of the medical apparatus with a thread.

According to one aspect of the invention, the female coupling portion may be formed integrally with a fluid line.

In this way no additional components are required for the connection to the fluid line and thus a simple and inexpensive configuration involving few components is possible.

In accordance with one aspect of the invention, the female coupling portion may include a second fastening portion.

In accordance with one aspect of the invention, the female coupling portion may be adapted to be fastened to a fluid line via the second fastening portion.

In accordance with one aspect of the invention, the second fastening portion of the female coupling portion may be a Luer lock which is adapted to be connected to a Luer lock of the fluid line.

According to one aspect of the invention, the second fastening portion of the female coupling portion may be a Luer lock having a male external cone which is adapted to be connected to a Luer lock having a female internal cone of the fluid line.

The fact that the female coupling portion is connected to the fluid line via the second fastening portion enables the coupling according to aspects of the invention to be used for already existing fluid lines as well. In other words, the female coupling portion may be screwed as a kind of connector onto a Luer lock of the fluid line, for example, and the female coupling portion thus connects the fluid line to the male coupling portion.

According to one aspect of the invention, the male coupling portion includes a preferably circumferential groove in which part of the female coupling portion engages.

According to one aspect of the invention, the male coupling portion includes a preferably circumferential groove in which at least a snap hook of the female coupling portion engages.

Thus, in a simple manner safe and tight connection between the male coupling portion and the female coupling portion may be established. It is of advantage when the female coupling portion is made from plastic material. Thus the female coupling portion may widen in the radial direction when being slipped onto the male coupling portion without being damaged. As soon as the snap hooks are level with the groove, they engage in the same and thus connect the two coupling portions. However, it is also possible to materialize the engagement via another snap-fit connection such as a ring snap-fit.

In accordance with one aspect of the invention, the male coupling portion and the female coupling portion can be connected to each other via a locking device.

In accordance with one aspect of the invention, the locking device may be provided on the male coupling portion.

In accordance with one aspect of the invention, the locking device may be provided on the female coupling portion.

Apart from the snap-fit connection, the locking device is another option of connecting the male and female coupling portions to each other. The locking device may be formed, for example, so that a pin operable via a lever may be guided into a groove. The locking device thus constitutes a safe connection without excessively loading the material of the female coupling portion or damaging the sealing element, for example.

In accordance with one aspect of the invention, the male coupling portion includes a stop or a shoulder which delimits the movement of the female coupling portion in the axial direction.

With the aid of the shoulder a predefined shifting distance of the female coupling portion can be fixed on the male coupling portion. If, for example, an afore-described configuration including a groove and a snap hook is used, the shoulder ensures that the snap hooks cannot be slid out of the groove and beyond the same, respectively, any more.

In accordance with one aspect of the invention, the male coupling portion and the female coupling portion can be released from each other by a release device.

In accordance with one aspect of the invention, the release device may be provided on the male coupling portion.

In accordance with one aspect of the invention, the release device may be provided on the female coupling portion.

In accordance with one aspect of the invention, the locking device and the release device exhibit a similar design.

It is thus possible to release the male and female coupling portions connected by engagement from each other again in a non-destructive manner by a release key or lever. Alternatively, connection and disconnection may also be realized by the locking and release device, respectively.

The medical system according to aspects of the invention contains a first fluid line and a medical apparatus and/or a second fluid line. In the first fluid line a first passage is provided and in the medical apparatus and/or in the second fluid line a second passage is provided. The first fluid line and the medical apparatus and/or the second fluid line may be connected to each other via a medical coupling according to aspects of the invention so that the first passage and the second passage are connected in a sealing manner.

In the medical system the medical coupling serves for interconnecting at least two fluid-guiding portions and, respectively, for establishing a connection so that fluid may flow from one line into a medical apparatus or into another line, or vice versa. Accordingly, the medical coupling may involve one or more of the afore-described aspects and, respectively, advantages.

Summing up, the medical coupling according to aspects of the invention and the medical system according to aspects of the invention help to improve the user friendliness, especially during use in renal replacement therapy, and to reduce set-up times. In addition, the bloodlines are prevented from twisting and a torque-independent connection is realized which cannot automatically come undone during therapy. Thus, time-consuming inspection and correction of the connection by the user is dropped, no unnoticed blood loss which might entail a risk for the patient will occur and mismeasurement of the pressures during the therapy can be prevented.

BRIEF DESCRIPTION OF THE DRAWINGS

The invention is best understood from the following detailed description when read in connection with the accompanying drawings. Included in the drawings are the following figures.

DETAILED DESCRIPTION OF PREFERRED EMBODIMENTS

Figure 1:
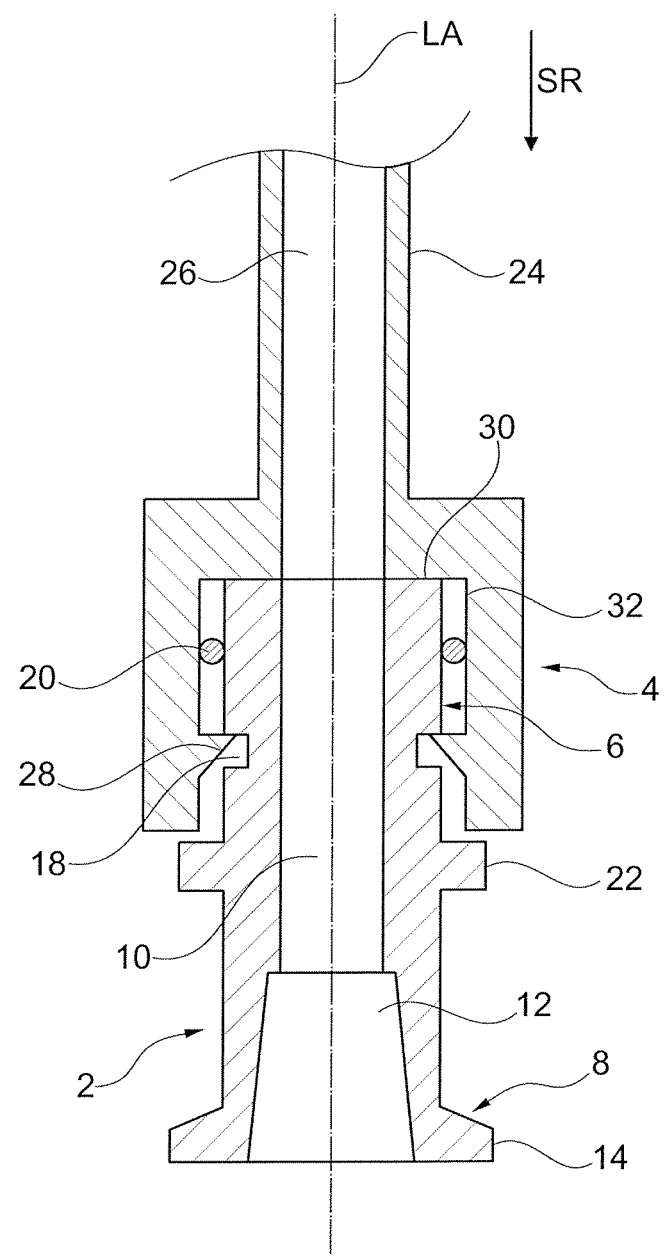
FIG. 1 illustrates a sectional view of an adapter including a coupling sleeve coupled thereto in accordance with a first embodiment.

FIG. 1 illustrates a first embodiment of a medical coupling according to aspects of the invention in which a substantially cylindrical adapter 2 and a coupling sleeve 4 are connected to each other. The adapter 2 includes a male coupling portion or, respectively, first coupling portion 6 on its end facing the coupling sleeve 4 and includes a first fastening portion 8 on the other end facing away from the coupling sleeve 4. In addition, the adapter 2 includes a continuous first passage 10 conically widening in the direction away from the coupling sleeve 4. In other words, a first female Luer lock internal cone 12 is formed. Furthermore, at the end of the first fastening portion 8 facing away from the coupling sleeve 4 a first external thread portion or first thread portion 14 is formed. Via the first female Luer lock internal cone 12 and the first thread portion 14 the adapter 2 can be fastened to a medical apparatus or device 16 (not shown in FIG. 1) such as a dialyzer or a machine for extracorporeal blood treatment. In the case of a dialyzer the blood-guiding lines are connected and in the case of a machine for extracorporeal blood treatment the pressure lines branching from the blood-guiding lines and guiding an air column to the pressure absorbers are connected. In other words, the adapter 2 can be fastened to each Luer lock of complementary design including a male external cone.

The first coupling portion 6 furthermore includes a circumferential groove 18. Moreover, an O-ring 20 is arranged between the groove 18 and the end of the first coupling portion 6 facing the coupling sleeve 4 as a sealing element. The O-ring 20 may contact the outer periphery of the first coupling portion 6, may be received in an additional sealing groove shown in FIG. 3 or may be formed, e.g. by 2K injection molding, integrally with the first coupling portion 6 as a sealing element. Additionally, a shoulder 22 which extends outwardly in the radial direction is formed at the end of the first coupling portion 6 facing away from the coupling sleeve 4 or, respectively, between the first coupling portion 6 and the first fastening portion 8.

The coupling sleeve 4 acts as a female coupling portion and is formed integrally with a fluid line or a tube 24 being connected to the end of the coupling sleeve 4 distant from the adapter 2. Inside the tube 24 and the coupling sleeve 4 a second passage 26 is formed. Further, plural snap hooks 28 evenly distributed in the peripheral direction are formed on the inner surface of the coupling sleeve 4. However, it is also possible that only one single circumferential snap hook is formed.

When the coupling sleeve 4 is slipped in the direction of a sliding direction SR, i.e. along a longitudinal axis LA of the adapter 2 and of the coupling sleeve 4 in the direction of the adapter 2, the snap hooks 28 abut on an end face 30 of the adapter 2 facing the coupling sleeve 4. This will result in the fact that the coupling sleeve 4 made from plastic widens in the radial direction and the coupling sleeve 4 is adapted to be slipped further in the sliding direction SR onto the adapter 2 and, respectively, the first coupling portion 6. As soon as the snap hooks 28 are level with the groove 18 in the axial direction, i.e. along the longitudinal axis LA, they engage in the groove 18 and the coupling sleeve 4 returns into its original position not widened in the radial direction. Accordingly, the O-ring 20 of the adapter 2 comes to rest on a sealing surface 32 on the inside of the coupling sleeve 4. Thus a dense flow path is formed between the first passage 10 of the adapter 2 and the second passage 26 of the coupling sleeve 4 and, respectively, the tube 24. Furthermore, the shoulder 22 delimits the movement of the coupling sleeve 4 in the sliding direction 4 so that the snap hooks 28 are retained in the groove 18 and thus the coupling sleeve 4 is safely connected to the adapter 2. However, certain axial play between the adapter 2 and the coupling sleeve 4 is permitted as long as the snap hooks 28 are not moved out of the groove 18 and the O-ring 20 rests on the sealing surface 32.

By the coupling or quick-connect coupling according to aspects of the invention not only a tight and force-independent connection of two fluid-guiding portions such as the coupling sleeve 4 including the tube 24 and the adapter 2 can be quickly established, but it is also possible, due to the radial sealing with the O-ring 20, that the coupling sleeve 4 and the adapter 2 may rotate relative to each other about the longitudinal axis LA. Thus the tube 24 is prevented from twisting or else the Luer lock between the adapter 2 and the medical apparatus 16 is prevented from disconnecting. It is also possible that the sealing element is provided in the coupling sleeve 4 and after connection gets into contact with a sealing surface of the adapter 2.

Figure 2:
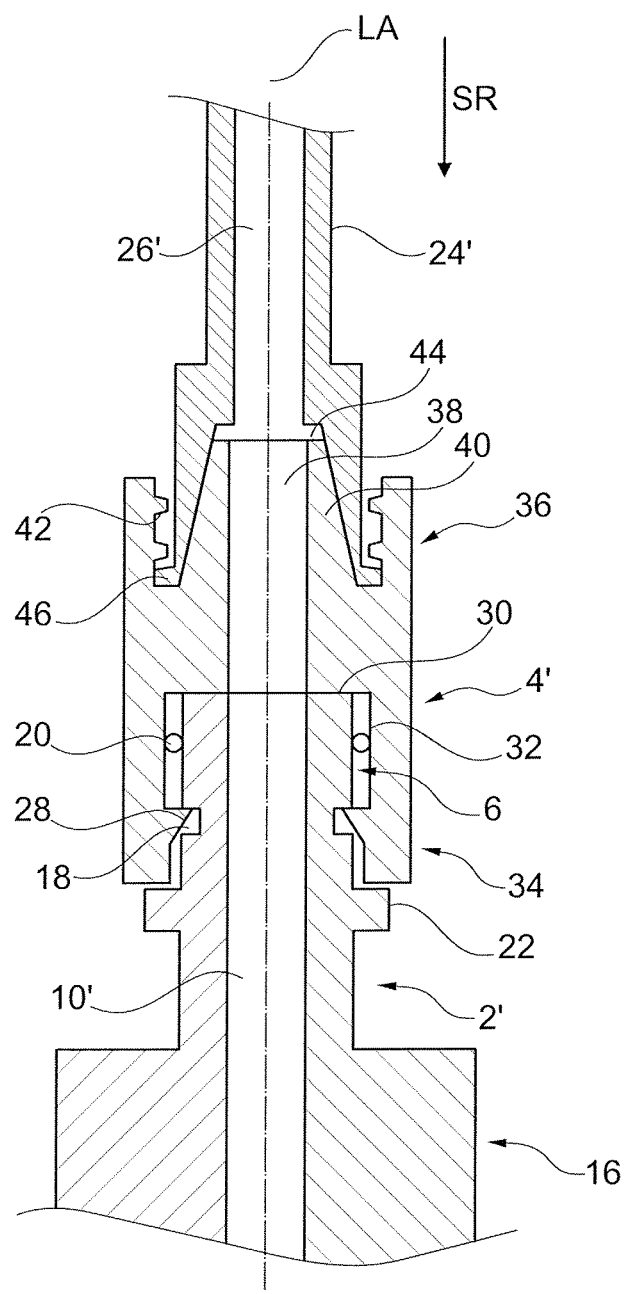
FIG. 2 illustrates a sectional view of a medical apparatus comprising a coupling sleeve coupled thereto according to a second embodiment.

FIG. 2 illustrates a second embodiment of a medical coupling according to aspects of the invention. Components equal to those of the first embodiment are provided with like reference numerals.

In the second embodiment, the adapter 2' is formed integrally with the medical apparatus 16. In other words, the adapter 2' rather is an extension of the medical apparatus 16 at the end of which facing the coupling sleeve 4' the first coupling portion 6 is formed as male coupling portion.

In the second embodiment the coupling sleeve 4' acts as a connector and thus connects the tube 24' to the medical apparatus 16. The coupling sleeve 4' comprises at its end facing the medical apparatus 16 a female coupling portion or, respectively, second coupling portion 34 and at its end facing the tube 24' comprises a second fastening portion 36. The connection of the adapter 2' and the coupling sleeve 4' and, respectively, the first coupling portion 6 and the second coupling portion 34 is made analogously to the first embodiment.

In the coupling sleeve 4' moreover a continuous third passage 38 is formed along the longitudinal axis LA. The second fastening portion 36 is a Luer lock. That is, the third passage 38 is enclosed by a male Luer lock external cone 40 extending in the direction of the tube 24'. In addition, at the radially outer end of the second fastening portion 36 an internal thread portion or, respectively, second thread portion 42 is provided.

The end of the tube 24' facing the coupling sleeve 4' is a Luer lock designed to be complementary to the Luer lock of the coupling sleeve 4'. In this way the second passage 26' conically widens toward the coupling sleeve 4'. In other words, a second female Luer lock internal cone 44 is formed. Moreover, at the end of the hose 24' facing away from the coupling sleeve 4' a second external thread portion or, respectively, third thread portion 46 is formed.

When the first coupling portion 6 and the coupling sleeve 4' are coupled, as afore-described, and in addition the tube 24' and the coupling sleeve 4' are interconnected via the Luer lock, a tight flow path can be provided from the second passage 26' in the tube 24' via the third passage 38 in the coupling sleeve 4' to the first passage 10' in the medical apparatus 16.

The afore-described embodiments illustrate various options as to how the tube 24 and the medical apparatus 16 can be connected to each other. However, further options of combining the various connections are possible as well. For example, the adapter 2 can be fastened, on the one hand, via a Luer lock to the medical apparatus and, on the other hand, can be engaged in the coupling sleeve 4' which is fastened to the tube 24' via a Luer lock.

Figure 3:
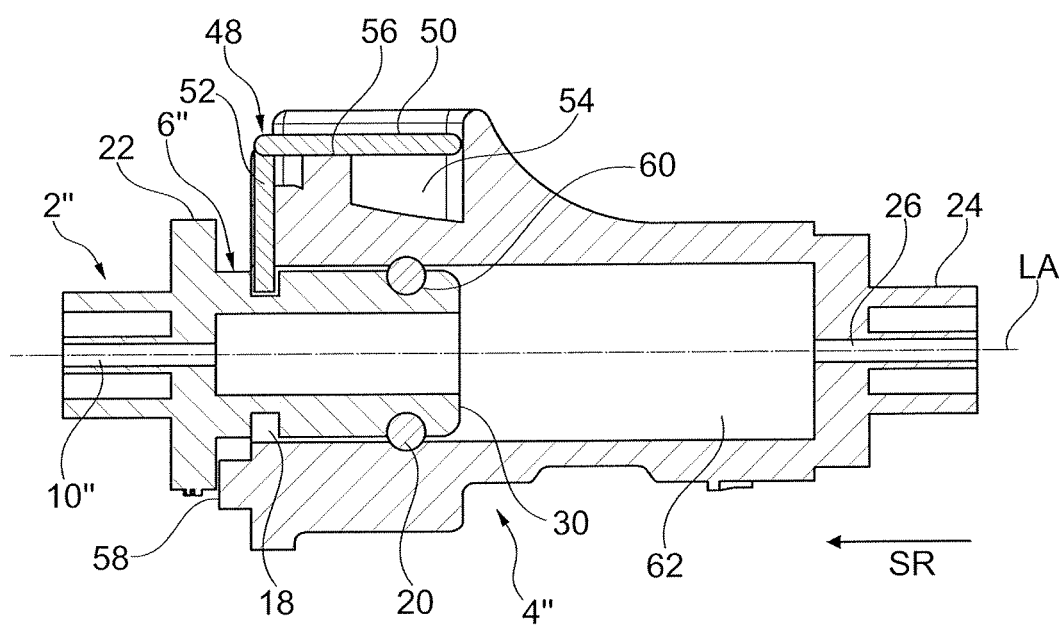
FIG. 3 illustrates a sectional view of an adapter comprising a coupling sleeve coupled thereto which includes a release device according to a third embodiment.

FIG. 3 illustrates a third embodiment of a medical coupling according to aspects of the invention. Components equal to those of the first and second embodiments are provided with like reference numerals.

In the third embodiment, the coupling sleeve 4" additionally includes a release device 48 comprising a lever 50 and a pin 52. In the locked state as shown in FIG. 3 the lever 50 is arranged in parallel to the longitudinal axis LA and the pin 52 is arranged perpendicularly to the longitudinal axis LA. The lever 50 is articulated at its end facing the adapter 2" to an end of the pin 52 facing away from the adapter 2". Furthermore, the release device 48 is provided in a recess 54 of the coupling sleeve 4" and is articulated to the coupling sleeve 4" via a pivoting point 56.

In order to be able to connect the coupling sleeve 4" to the adapter 2" the lever 50 has to be moved inwardly in the radial direction at its end facing away from the adapter 2". In this way the pin 52 is moved outwardly in the radial direction and the coupling sleeve 4" can be slipped in the sliding direction SR onto the adapter 2" and, respectively, the first coupling portion 6". As soon as a front boundary area 58 of the coupling sleeve 4" facing the adapter 2" abuts against the shoulder 22, the groove 18 is level with the pin 52 in the axial direction. When the lever 50 is released, i.e. is no longer actuated, the lever returns into its home position in parallel to the longitudinal axis LA and the pin 52 moves into the groove 18 so that the adapter 2" and the coupling sleeve 4" are connected to each other. For releasing the connection the lever 50 in turn has to be actuated, namely, moved inwardly in the radial direction. In this way the pin 52 moves out of the groove 18 and the coupling sleeve 4" may be removed from the adapter 2" against the sliding direction SR.

The coupling is thus designed to be releasable in the axial direction. However, this can also be realized via a release key or the like instead of via a release lever. In the afore-described third embodiment the unlocking device 48 is disposed on the coupling sleeve 4". It is also possible, however, to dispose the release device 48 on the adapter 2".

Hereinafter, several differences and advantageous configurations of the third embodiment as compared to the first and second embodiments will be described.

In the third embodiment the O-ring 20 is received in a sealing groove 60. In this way, the radial extension of the sealing element is delimited. This configuration may also be used in the first and second embodiments, as advantageously in this way the snap hooks 28 are adapted to properly slide over the O-ring 20 when the coupling sleeve is slipped on.

Moreover, in the third embodiment the end face 30 of the adapter 2" is not directly adjacent to the coupling sleeve 4". Rather, a radially outwardly widened receiving opening 62 in which the first coupling portion 6" can be received is connected to the second passage 26 in the direction of the adapter 2". The first passage 10", too, is widened outwardly in the radial direction toward the coupling sleeve 4".

Further, not only one release device 48 has to be provided in the third embodiment. There may also be distributed two or more thereof preferably evenly in, the peripheral direction. In addition, the adapter 2" of the third embodiment either may be adapted to be fastened, analogously to the adapter 2 of the first embodiment, to the medical apparatus 16 or may be formed integrally with the medical apparatus 16 analogously to the adapter 2' of the second embodiment.

The invention claimed is:

1. A medical coupling for fluid-tight connection of two fluid-guiding portions in medical applications, the medical coupling defining a longitudinal axis and comprising:
    a male coupling portion having a continuous first passage and an outer periphery; and
    a female coupling portion adapted to be slipped over the male coupling portion and having a continuous second passage and an inner periphery;
    wherein a circumferential radial sealing is provided on at least one of the outer periphery of the male coupling portion or the inner periphery of the female coupling portion;
    wherein the male coupling portion includes a shoulder or a stop, which delimits movement of the female coupling portion in an axial direction and provides for a pre-defined shifting distance of the female coupling portion on the male portion;
    wherein the medical coupling is an axially lockable quick-connect coupling; and
    wherein the male coupling portion and the female coupling portion are connected to each other by a locking device comprising a pin having a long dimension extending radially inwardly toward the longitudinal axis of the medical coupling and a groove, the pin comprising a first end articulated to an end of a lever and a second end configured to fit into the groove.

2. The medical coupling according to claim 1, wherein:
    the male coupling portion is formed integrally with a medical apparatus.

3. The medical coupling according to claim 1, wherein:
    the male coupling portion includes a first fastening portion; and
    the male coupling portion is adapted to be fastened to a medical apparatus via the first fastening portion.

4. The medical coupling according to claim 3, wherein:
    the first fastening portion of the male coupling portion is a first Luer lock that is connectable to a second Luer lock of the medical apparatus.

5. The medical coupling according to claim 4, wherein the first Luer lock comprises a female internal cone and the second Luer lock comprises a male external cone.

6. The medical coupling according to claim 5, wherein:
    the female coupling portion includes a second fastening portion adapted to be fastened to a fluid line;
    the second fastening portion of the female coupling portion is a third Luer lock that is connectable to a fourth Luer lock of the fluid line; and
    the third Luer lock comprises a male external cone and the fourth Luer lock comprises a female internal cone.

7. The medical coupling according to claim 1, wherein:
    the female coupling portion is formed integrally with a fluid line.

8. The medical coupling according to claim 1, wherein:
    the female coupling portion includes a fastening portion; and the female coupling portion is adapted to be fastened to a fluid line via the fastening portion.

9. The medical coupling according to claim 8, wherein:
the fastening portion of the female coupling portion is a first Luer lock that is connectable to a second Luer lock of the fluid line.

10. The medical coupling according to claim 9, wherein:
the first Luer lock comprises a male external cone and the second Luer lock comprises a female internal cone.

11. The medical coupling according to claim 1, wherein:
the male coupling portion includes a circumferential groove configured to engage a part of the female coupling portion.

* * * * *